(12) United States Patent
Boggett et al.

(10) Patent No.: US 6,259,936 B1
(45) Date of Patent: Jul. 10, 2001

(54) APPARATUS FOR IMAGING BLOOD FLOW IN THE MICROCIRCULATION

(75) Inventors: David Boggett, Devon; Xiabing Huang, Somerset, both of (GB)

(73) Assignee: Moor Instruments Limited, Devon (GB)

( * ) Notice: Subject to any disclaimer, the term of this patent is extended or adjusted under 35 U.S.C. 154(b) by 0 days.

(21) Appl. No.: 09/367,667

(22) PCT Filed: Feb. 18, 1998

(86) PCT No.: PCT/GB98/00503

§ 371 Date: Oct. 25, 1999

§ 102(e) Date: Oct. 25, 1999

(87) PCT Pub. No.: WO98/36685

PCT Pub. Date: Aug. 27, 1998

(30) Foreign Application Priority Data

Feb. 19, 1997 (GB) .................................. 9703416

(51) Int. Cl.⁷ ....................................... A61B 6/00
(52) U.S. Cl. .................. 600/310; 600/322; 600/328; 600/807; 600/473; 600/475; 600/476; 604/20
(58) Field of Search ................. 600/310, 322, 600/328, 407, 473, 475, 476, 477, 504; 604/20; 356/4.01

(56) References Cited

U.S. PATENT DOCUMENTS

| | | | |
|---|---|---|---|
| 5,736,410 | * 4/1998 | Zarling et al. | 436/172 |
| 5,807,261 | * 9/1998 | Benaron et al. | 600/473 |
| 5,813,987 | * 9/1998 | Modell et al. | 600/473 |
| 5,845,639 | * 12/1998 | Hochman et al. | 356/39 |

FOREIGN PATENT DOCUMENTS

| | | |
|---|---|---|
| 0 488 614 | 6/1992 | (EP) . |
| 0 488 615 | 6/1992 | (EP) . |
| WO 97/43950 | 11/1997 | (WO) . |

\* cited by examiner

*Primary Examiner*—Marvin M. Lateef
*Assistant Examiner*—Jeoyuh Lin
(74) *Attorney, Agent, or Firm*—Barry R. Lipsitz

(57) ABSTRACT

Blood perfusion in tissue is imaged using a beam from a monochromatic laser light source that is scanned over the tissue surface in a predetermined pattern at a substantially constant speed. Light scattered from the tissue surface is collected. The position of the beam can be determined and recorded at any point of the scan, and the beam can be halted at a predetermined position or positions during the scan. Two or more photodetectors are positioned to collect light diffusely scattered from the tissue surface such that specularly reflected light is detected by either no detector or by only one detector at a given time. Electrical signals from the photodetectors are processed, and saturation of a photodetector is registered. The saturated photodetector is eliminated from the signal processing to ensure that only unsaturated photodetector signals are processed. The blood perfusion measurements are recorded and displayed.

10 Claims, 11 Drawing Sheets

APPARATUS FOR IMAGING BLOOD FLOW IN THE MICROCIRCULATION

The present invention relates to an apparatus for the measurement and imaging of particle movement and flow in fluids, particularly for the measurement and imaging of blood flow in the small superficial blood vessels of body tissue.

Blood flow in the small blood vessels of the skin performs an essential role in the regulation of the metabolic, hemodynamic and thermal state of an individual and the condition of the microcirculation over both long and short time periods can reflect the general state of health. The degree of blood perfusion in the cutaneous microvascular structure often provides a good indicator of peripheral vascular disease and reduction of blood flow in the microcirculatory blood vessels can often be attributed to cutaneous vascularisation disorders; so there are many situations in routine clinical medicine where measurement of the blood flow is important.

The microcirculation, its responses to stimuli, and its response to therapeutic regimes, were not open to routine continuous assessment and investigation until the introduction of the laser Doppler technique in the 1970's and subsequent developments in the 1980's.

The technique depends on the Doppler principle whereby laser light which is incident on tissue, typically the skin surface, is scattered by moving red blood cells and undergoes frequency broadening. The frequency broadened laser light, together with laser light scattered from static tissue, is photodetected and the resulting photo current processed to provide a signal which correlates with blood flow.

Perfusion measurements using single and multiple channel fibre optic laser Doppler monitors have been made on practically all tissues and applied in most branches of medicine and physiology. The technique and its application has been described in numerous publications. A representative selection of these are included in 'Laser—Doppler Blood Flowmetry', ed. A. P. Shepherd and P. Å. Oberg, Kluwer Academic Publishers 1990 and also 'Laser Doppler' ed. G. V. Belcaro, U. Hoffmann, A. Bollinger and A. N. Nicolaides, Med-Orion Publishing Co. 1994.

The application of these principles to measurements in the microcirculation was described by M. D. Stern in Nature Vol 254, 56, March 1975, 'In vivo evaluation of microcirculation by coherent light scattering'; M. D. Stern et al 1977 'Continuous measurement of tissue blood flow by laser-Doppler spectroscopy' Am J. Physiol 232: H441–H448; and subsequently in U.S. Pat. No. 4,109,647.

For some clinical applications, such as plastic surgery and wound healing, point measurements using optic probes attached to the skin are severely limited and this has prevented widespread application in these areas. Three reasons for this are: point to point variation (spatial variability) requiring several readings to give reliable measurement, contact between the probe and the tissue surface, and interference from fibre movements which degrade the measurements.

These problems have been mainly overcome by the development of laser Doppler scanners which map perfusion over an area of tissue, typically 100 cm$^2$ and in some cases over 1000 cm$^2$, using a scanning laser beam and one or more photodetectors. EP-A-0282210 describes an apparatus for monitoring blood stream in the skin surface which employs a linear sensor comprising a plurality of light receiving elements to receive the laser light reflected by the skin surface, memory means for storing the output signals from the light receiving elements and calculating means for processing these signals to derive information about the blood stream. The blood stream velocity or distribution information may thereby be calculated and displayed. WO90/11044 describes a method of determination of blood flow and an apparatus for use therein which involves projecting a beam of laser light to move over a surface beneath which blood flow in a vessel or vascular bed is to be determined, collecting the reflected and scattered light, measuring a spectrum of frequencies in the collected light and determining from differences in the frequencies the blood flow beneath the surface under examination. WO91/06244 describes a system which includes means for directing a laser beam onto a body part to be examined and for guided movement of the laser beam through a series of measurement points over the body part in accordance with a predetermined scanning pattern. The laser beam is halted at each measurement point for a given time interval. These devices have found many research applications and have generated considerable clinical interest.

A serious problem which affects the production of images using these prior art laser Doppler imagers arises when the surface of the target area is highly reflective. Normally, the illumination of the surface of tissue with a beam of laser light will result in light being scattered from the surface and from the tissue below the surface.

Generally, the light is diffusely scattered so that only a very small fraction of the incident light would be detected by a photodetector "viewing" the surface, typically at a distance from the surface of several tens of centimeters. When the surface of the target area is highly reflective, for instance skin which is wet, oily or greasy or which is covered by a transparent or translucent dressing or the surface of an organ exposed during open surgery, a large fraction of the incident light is specularly reflected. If this specularly reflected light is photodetected a high photo current will be generated by the photodetector, e.g., photodiode, resulting in signal saturation of the current-to-voltage converter or current amplifier used and the consequent loss or impairment of image information.

Conditions necessary for photodetection of this specularly reflected light depend on the orientation of the reflecting surface relative to the incident beam and the position of the photodetector so that as the laser beam is scanned over the surface the condition of high detected light intensity and loss of image information occurs over a range of beam angles. In general the larger the effective photodetector, which can for example be increased by the use of a lens, the larger the area of image affected. Both the flux and light intensity (photo image) are affected.

The present invention seeks to reduce significantly or even eliminate the effects of specular reflection thus enabling measurements of intensity and blood flow (flux) to be made when one photodetector is saturated.

The present invention provides an apparatus for imaging blood perfusion in tissue which comprises:
  a monochromatic laser light source;
  means for irradiating a section of the surface of the tissue with monochromatic light from the light source;
  means for collecting light scattered from the irradiated section;
  means for scanning a beam of the monochromatic laser light over the tissue surface in a predetermined pattern;
  means for scanning the beam at substantially constant speed across the tissue;
  means for determining and recording the position of the beam at any point of the scan;

means for halting the beam at a predetermined position or positions during the scan;

two or more photodetectors positioned to collect light diffusely scattered from the tissue surface and so positioned to ensure that specularly reflected light is detected by either no detector or by only one detector at a given time;

means for processing the electrical output signals from the photodetectors;

means for registering saturation of a photodetector and eliminating the saturated photodetector signal from the signal processing ensuring that only photodetector signals which are unsaturated are processed; and means for recording and displaying the blood perfusion measurements.

Compared to the prior art laser Doppler imagers the apparatus of the present invention is able to provide images of blood perfusion in tissue when the tissue has a highly reflective surface.

The apparatus of the present invention includes a monochromatic laser light source for generating the laser beam used for irradiating a section of the tissue surface. The laser used has a wavelength in the visible or near infra-red part of the optical spectrum. The power of the laser is typically 1 to 2 mW and the light generated must be highly monochromatic and stable. The beam diameter is typically 1 mm.

The laser beam is directed to the desired position on the tissue surface by means of reflection from either a single front silvered mirror which is mounted in a gimbal allowing rotation about orthogonal axes or by a pair of front silvered mirrors one which rotates about a vertical axis and the other about a horizontal axis.

For a single mirror system the orthogonal axes lay in the silvered face of the mirror and pass through the mirror centre. The laser beam is directed at the mirror centre and is incident at this point for changing angles of incidence as the mirror rotates. The mirror acts as both a reflector for the incident beam and a reflector for some of the light scattered from the tissue site as illustrated in FIG. 4. The pair of lenses increase the effective photodetector area, increasing signal to noise and, thus, increasing the tissue surface/photodetector distance for which satisfactory measurements of blood flow can be made.

For this optical arrangement the image of the laser spot on the tissue surface produced by reflection in the mirror lies along the straight line along which the laser beam travels as it passes between the photodetector and lenses. The image lies on this line whatever the tissue surface/mirror distance thus making it easy to predict the location of the laser spot images formed by the lens. These images, or part of each one, are incident on the photodetector for a range of lens/tissue distances, typically 0.2 to 2 m.

If lenses are not used then the tissue surface/mirror distance for acceptable signal to noise is more limited though the optics is simplified. An example of such a system is illustrated in FIG. 3.

The angular position of the mirror relative to the incident laser beam can be controlled using dc servo motors or stepper motors or a combination of both. High resolution shaft encoders, coupled directly to the mirror drive to reduce the effects of backlash in the motors, provide accurate and reliable monitoring of the mirror position and hence the laser spot position on the tissue surface. This data from the shaft encoders, pulse counts and pulse rates, enable position and scan speed to be computer controlled.

For rapid scanning of the beam a constant speed mode of scanning is used. This requires dc servo motors with Proportional Integral and Differential control (PID) of speed and position which can be provided by a combination of hardware and software using standard control systems. Angular speeds of the order of 5 rev/min 130° per second) are used for a fast scan. If 250 measurements are made during one line scan the time interval between measurements is 4 ms. Slower scan rates can be programmed. Slow scan rates, typically about 2° per second, with 50 to 60 ms between measurements have the advantage that lower Doppler shift signals can be processed and longer integration times used to improve signal to noise.

A scanning sequence could be as follows:

From rest a short period of angular acceleration takes the mirror to a target constant angular velocity; a line is scanned at constant velocity, and a final short period of deceleration brings the mirrors to rest. For rotation about a vertical axis the laser spot will trace out an appropriate horizontal line on the tissue surface, say from right to left. The mirror is then rotated about a horizontal axis through a predetermined angular increment, e.g., 0.1°. The acceleration, constant speed, deceleration phases are repeated but now from left to right.

By scanning the beam in this raster fashion a series of measurements can be made; and, by colour coding the flow measurements, a colour image of blood flow distribution over the scanned surface can be displayed, for instance on a pc monitor screen. Single point measurements can be made by halting the beam for an indefinite or predetermined time. Colour coded images can be built up from a series of single point measurements taken from different points on the tissue surface. Also flux/time graphs can be recorded and displayed.

Single point measurements give a high temporal resolution (40 Hz data rates are typical) enabling rapid blood flow changes to be recorded, whereas the laser Doppler imager can provide spatial information and has the ability to average blood flow measurements over large areas.

The apparatus requires the use of two or more photodetectors with sufficient separation between them to ensure that at any given time during an image scan at least one detector is unsaturated. It is this detector (or these detectors when more than two photodetectors may be used) which will be used to measure flux and intensity. The signals generated by any saturated photodetector will be rejected. The light scattered from the tissue may be detected directly by the photodetectors or may be imaged onto the photodetector(s) by a suitable lens.

Typical photodetectors suitable for laser Doppler measurement have areas of a few mm². It is convenient to increase the effective photodetector area using a convex lens as this increases the signal to noise enabling blood flow measurements to be done with distances of a meter or more between the scanner and the tissue surface. With a 2 mW laser giving a beam diameter of 1 mm, measurements can be made using a scanner/tissue surface separation of 2 m using a pair of 50 mm diameter convex glass lenses for light collection.

The invention will now be described, by way of example only, with references to the accompanying drawings of which:

Figure 1A:
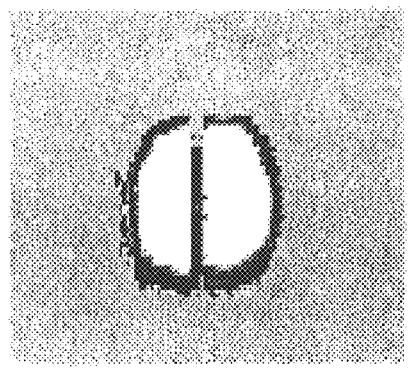
FIG. 1 shows images recorded from a scan of a layer of milk using a prior art laser Doppler imager.
Figure 1B:
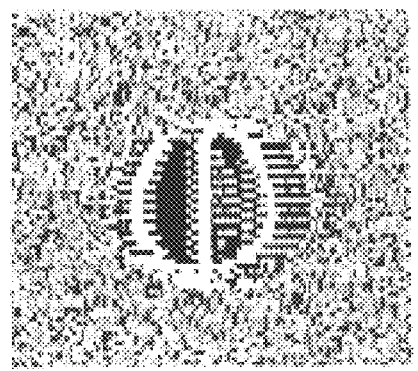
Figure 2A:
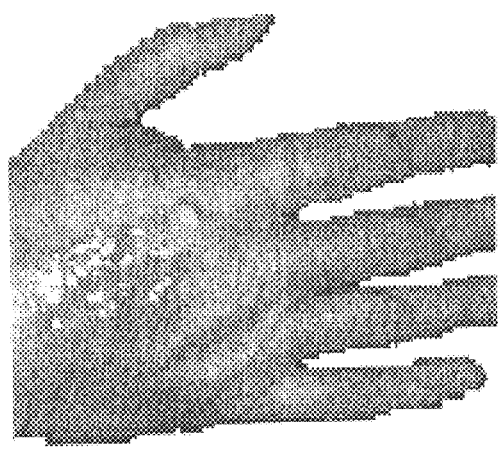
FIG. 2 shows images recorded from a scan of the back of a hand, which has a highly reflecting clear gel smeared on part of it, using a prior art laser Doppler imager.
Figure 2B:
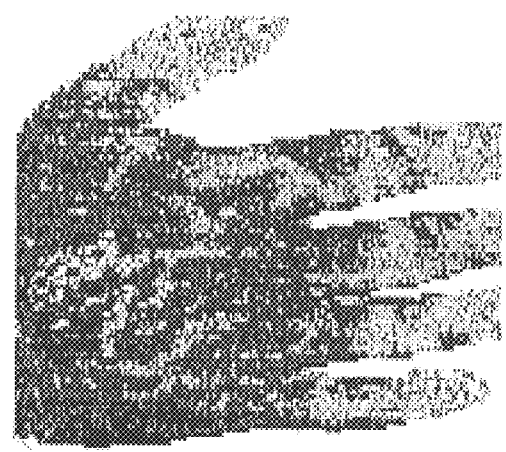

As shown in FIG. 1 a scan of a layer of milk using a prior art laser Doppler imager produced a photoimage having white areas which indicate amplifier saturation and/or intensity values outside the normal range for which the imager is designed. There are corresponding areas on the flux image. Indeed, a larger area may be affected as there is a time delay during which the flux signal processor recovers from saturation. The two large white areas in the photo image result from the flat mirror-like surface of the milk and their shape is the result of using a pair of lenses to collect the light. When blood flow in wet tissue is imaged the saturation areas may be smaller and greater in number than in the case of the milk layer because the surface of the wet tissue is less mirror-like. The flux and photo images in FIG. 2, from the back of a hand smeared with a clear gel, illustrate this.

Figure 3:
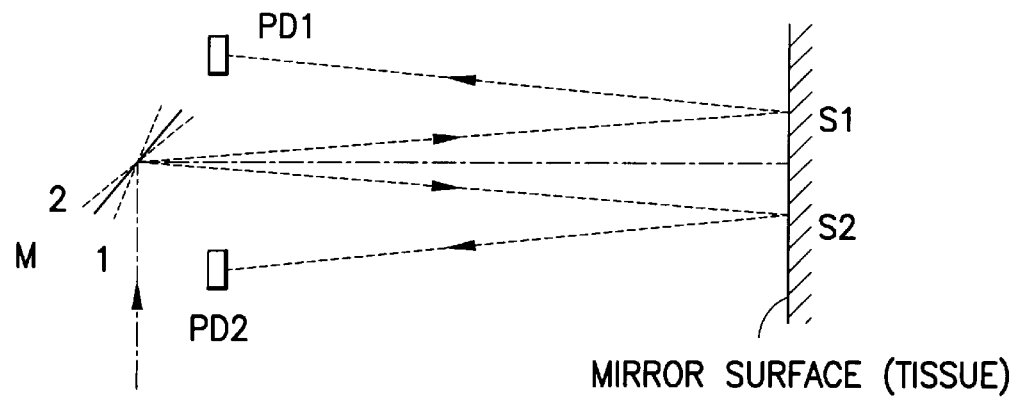
FIG. 3 is a diagram of an optical system having two photodetectors illustrating saturation.

An example of a suitable two photodetector optical system is shown in FIG. 3. In this, a simple laser beam scanning system is illustrated whereby a collimated laser beam can be directed to a tissue surface by rotating a front silvered flat mirror (M). If the tissue surface is replaced by another flat mirror it can be seen that if the beam is incident at point S1 specularly reflected light will be incident on the detector PD1 and if the beam is incident at point S2 reflected light will be incident on detector PD2. Generally, during a scan neither detector is saturated and if saturation does occur only one of the two detectors is affected. If each detector is provided with a light collecting lens, to increase its effective area, saturation will recur over a range of angles of incidence though again only one detector at a given time will be saturated.

Photodetectors suitable for laser Doppler measurement typically have collecting areas of a few $mm^2$. The effective photodetector area may be increased using a convex lens as this increases the signal to noise enabling blood flow measurements to be made with distances of a meter or more between the scanner and the tissue surface. Using a 2 mW laser with a beam diameter of 1 mm, measurements can be made with scanner/tissue surface separation of 2 m using a pair of 50 mm diameter convex glass lenses for light collection.

Figure 4:
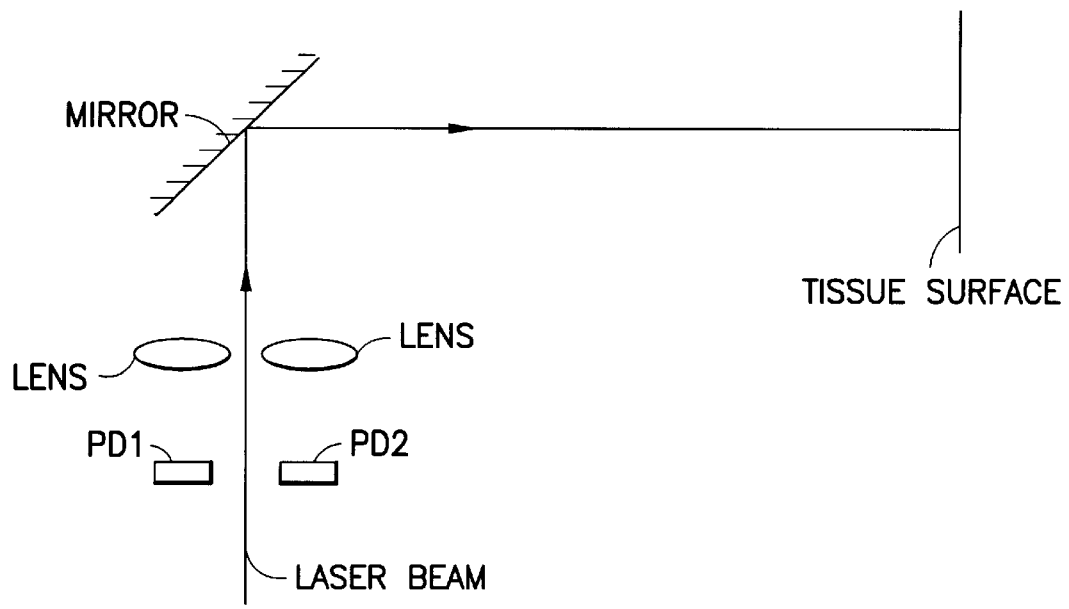
FIG. 4 is a diagram of another optical system that may be employed according to the present invention.
Figure 5A:
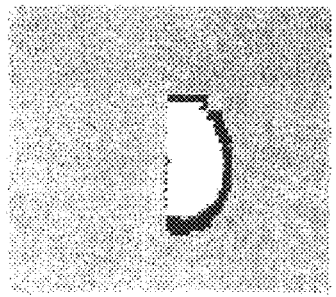
FIG. 5 shows images recorded from a scan of a layer of milk using the optical system shown in FIG. 4.
Figure 5B:
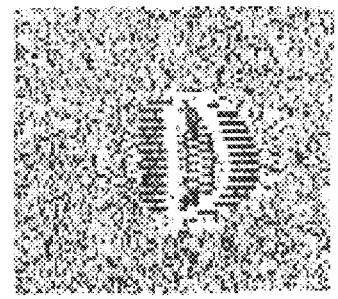
Figure 5C:
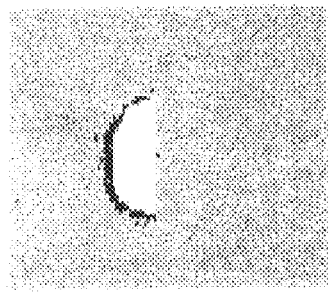
Figure 5D:
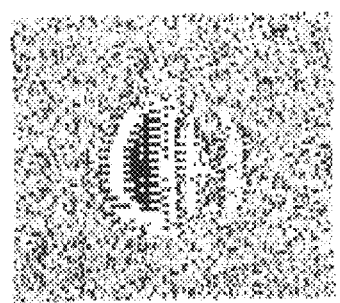

An optical system which uses a large area mirror to direct the laser beam to the tissue surface and which also reflects a small fraction of the diffuse light scattered from the tissue to a pair of photodiodes, via collecting lenses, is shown in FIG. 4. This optical arrangement ensures that the image, or part of the image, of the laser spot is on both photodetector surfaces for a wide range of distances between scanner and tissue (typically 0.2 to 2 m). For diffusely scattered light the photodetectors are approximately equally illuminated. However, if specular reflection occurs only one photodetector at a given time will be illuminated by intense light. Images recorded with one photo detector $PD_1$ covered by an opaque screen, so that only the other photo detector $PD_2$ is active as a detector, are shown in FIG. 5a. FIG. 5b shows images of a scan of a layer of milk recorded with $PD_1$ active and $PD_2$ covered.

Figure 6:
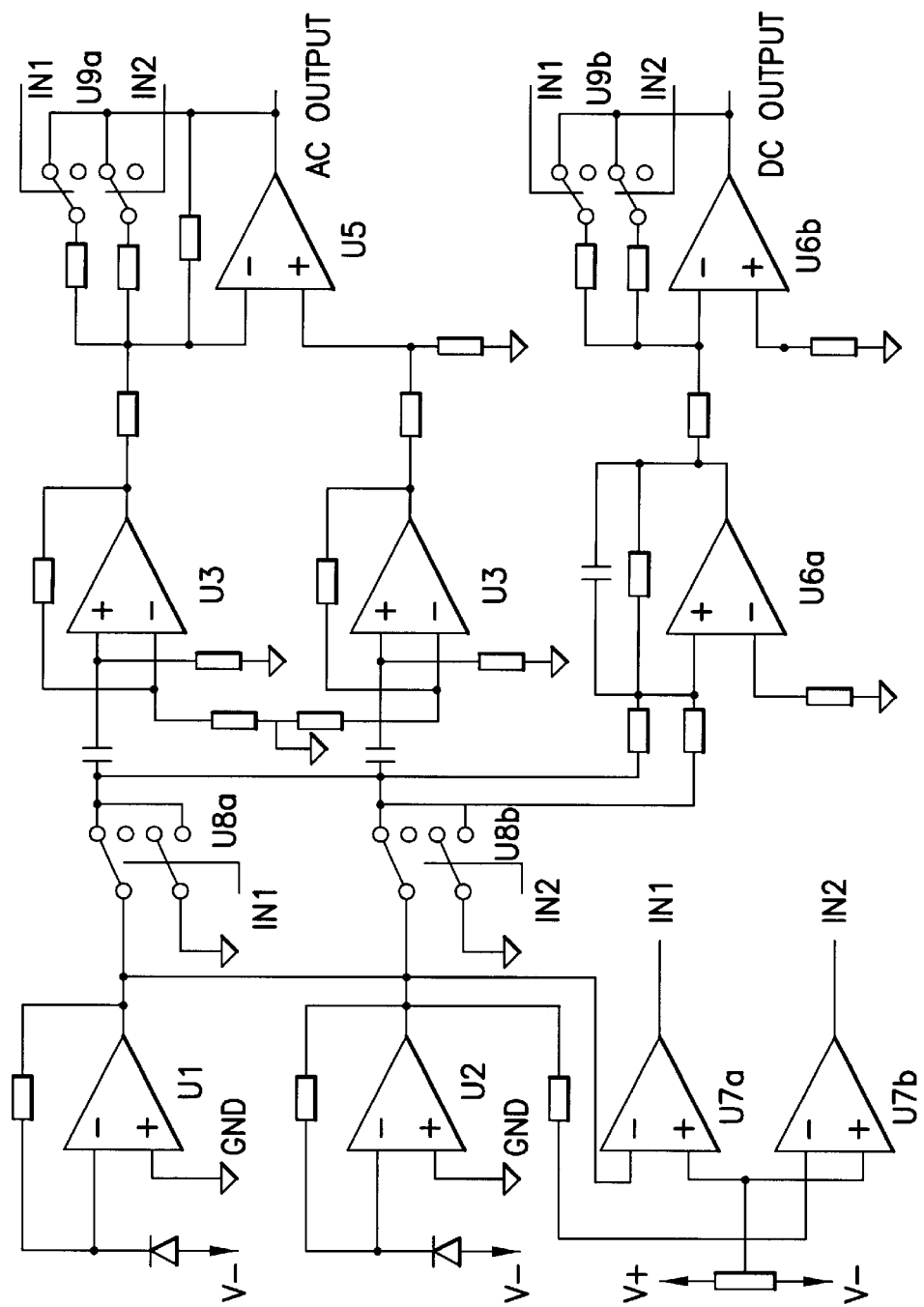
FIG. 6 is a diagram of a circuit which rejects a high intensity photodetected signal which causes saturation for use in the present invention.

A circuit which rejects a high intensity photodetected signal which causes saturation, and enables measurements to be made for both saturation and non-saturation conditions, is shown in FIG. 6. This is a two channel photodetector amplifier circuit which generates (1) an ac signal proportional to the square root of the sum of the squares of the ac components of the two photo current signals and (2) a dc signal proportional to the sum of the dc components of the photo detector signals.

U1 and U2 are current-to-voltage converters, U3, U4 and U5 act as a high pass amplifier which combines the two photo current ac signals, U6 adds and low pass filters the two photo current dc signals and U7 is a discriminator which registers a saturation condition in one or other of the photo current-to-voltage converters. U8 and U9 are analogue switches controlled by the outputs IN1 and IN2 of the discriminator.

The switches are configured so that if U1 is saturated (high $V_1$) the signal paths to U3 and U5 are grounded and only the photo signal from $PD_2$ is processed, and vice versa if U2 is saturated. To maintain constant outputs for constant flux and dc inputs ac and dc gains are automatically switched when saturation occurs.

Figure 7A:
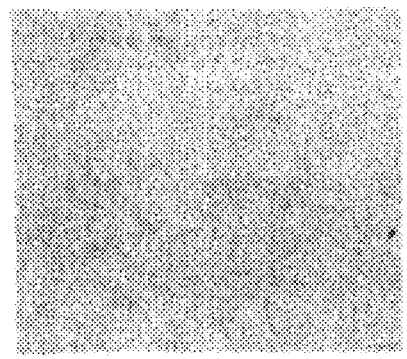
FIG. 7 shows images recorded from a scan of a layer of milk using an apparatus of the present invention employing the signal rejection circuit shown in FIG. 6.
Figure 7B:
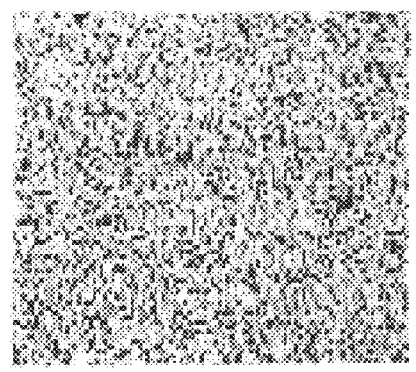

FIG. 7 shows images of a scan of a layer of milk recorded with the high intensity signal rejection circuit in operation. The high intensity regions recorded in FIG. 1 and in FIGS. 5a and 5b have been eliminated.

Switching of the ac and dc gains is not necessary if appropriate signal scaling is performed in a later stage of the signal processing. For example, at a high level of software, on a pc, or in the instrument's dedicated digital processor.

Figure 8:
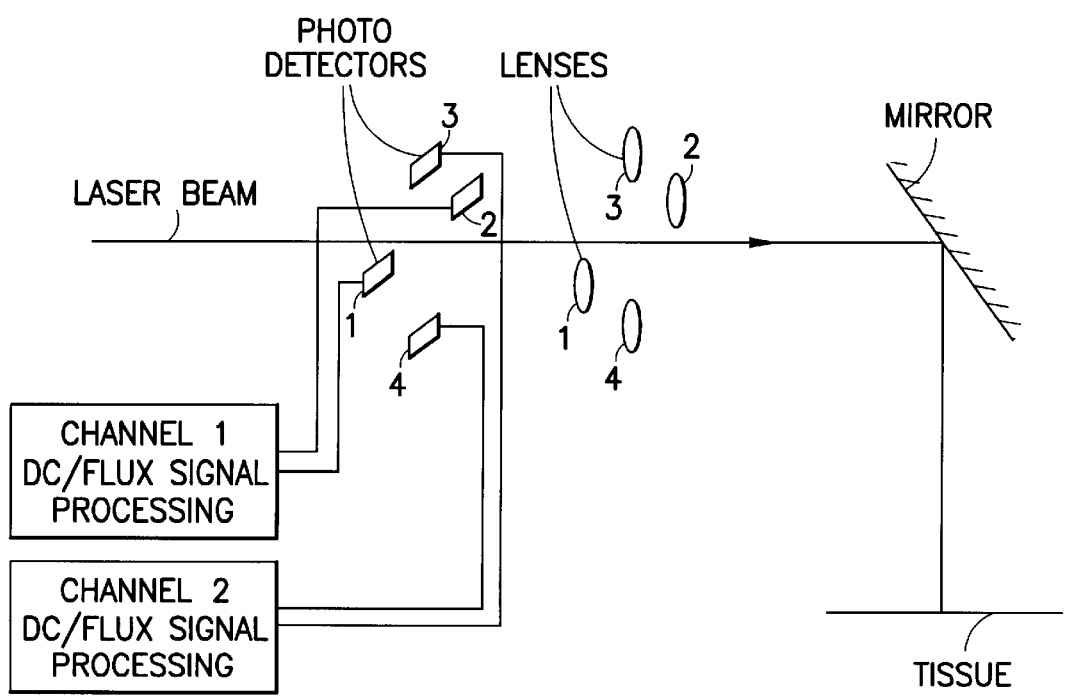
FIG. 8 is a diagram of an optical system having two pairs of photodetectors that may be employed in the apparatus of the present invention.

Some additional advantages can be achieved by using two pairs of photodiodes. Signal to noise is increased by a factor of $\sqrt{2}$ much of the switching circuitry of FIG. 6 is not needed. An example of such a two channel arrangement is shown in FIG. 8. In FIG. 8 the photodiodes are paired to provide essentially a system with two independent channels. As with the two photodiode system at any one time during a scan only one detector will be saturated and hence only one pair will be affected.

A variation of the system would be to store and display both of the flux images generated by the two channels. The regions of saturation, being easily identifiable, can then be eliminated by post detection processing and the images combined to produce a saturation free blood flow image.

In normal conditions of non-saturation the outputs of the two channels are summed and averaged. When saturation occurs only the unaffected channel is used to generate an output. This system will be software controlled and hence will not require the signal switching circuit of FIG. 6. However, because signal integration is used to improve signal to noise in the final stages of the system's analogue processor it is necessary to switch the time constant of this integrator to a low value (e.g., 1 ms). This enables the integrator to return to its normal state within a few ms after saturation. The switching signals can be generated by discriminator of the type shown in FIG. 6.

The apparatus of the present invention is provided with means for processing the photo current signals to produce blood flow (flux) and intensity signals at each point in an image scan and means for displaying the blood perfusion measurements, for instance, producing an image display of blood flow in the tissue surface and a photo image derived from the measured intensity variations.

The first moment of the power spectral density of the photo current produced by the heterodyne mixing of Doppler shifted and unshifted laser light scattered from the microvascular is commonly used as a measure of perfusion. This parameter is usually referred to as 'Flux'. Theoretical and experimental models of laser scattering from red blood cells (rbc) and biological tissue were made by R. Bonner and R. Nossal June 1981, Vol 20 No 12 Applied Optics 'Model for laser Doppler measurements of blood flow in tissue'. They showed that for Flux = (rbc average speed) × (rbc number concentration)

$$= \int_{\omega_1}^{\omega_2} \omega P(\omega) d\omega, \quad \omega = 2\pi f$$

where $\omega$ is the angular frequency of a Doppler shift (f is the frequency in Hz)

$P(\omega)$ is the power spectral density of the photo current and $\omega_1$ and $\omega_2$ are the lower and upper frequencies of the band of the Doppler broadened signals processed.

$f_1$ is typically 20 Hz and $f_2$ between 10 KHz to 20 KHz.

This flux has a fundamental noise component due to dark and shot noise and its magnitude is proportional to the square of the laser beam power.

For a given point on the tissue surface, which is irradiated by the laser beam, the intensity of the scattered light as measured by the photodetectors is directly proportional to the average photo current $I_{dc}$ (the dc direct photo current). Normalisation is performed by dividing the flux signal by a quantity proportional to $I_{dc}^2$ after noise has been subtracted.

Noise=Dark+Shot, Dark=Constant$_1$

Shot=Constant$_2$×$I_{dc}$ $$\text{Normalised Flux} = \left( \int_{\omega_1}^{\omega_2} \omega P(\omega) d\omega - \text{Noise} \right) / I_{dc}^2$$

The processing of the photo currents can be carried out using analogue circuits. This requires a suitable photodetector, usually a pin type silicon photodetector, a high gain current to voltage converter, high pass filter followed by low pass to pass the spectrum of current frequencies in the band $\omega_2$–$\omega_1$ (e.g., a band of 15 KHz).

These signals are then filtered through an $\omega^{1/2}$ filter, then squared and integrated with a time constant appropriate for the scan speed used.

Figure 9A:
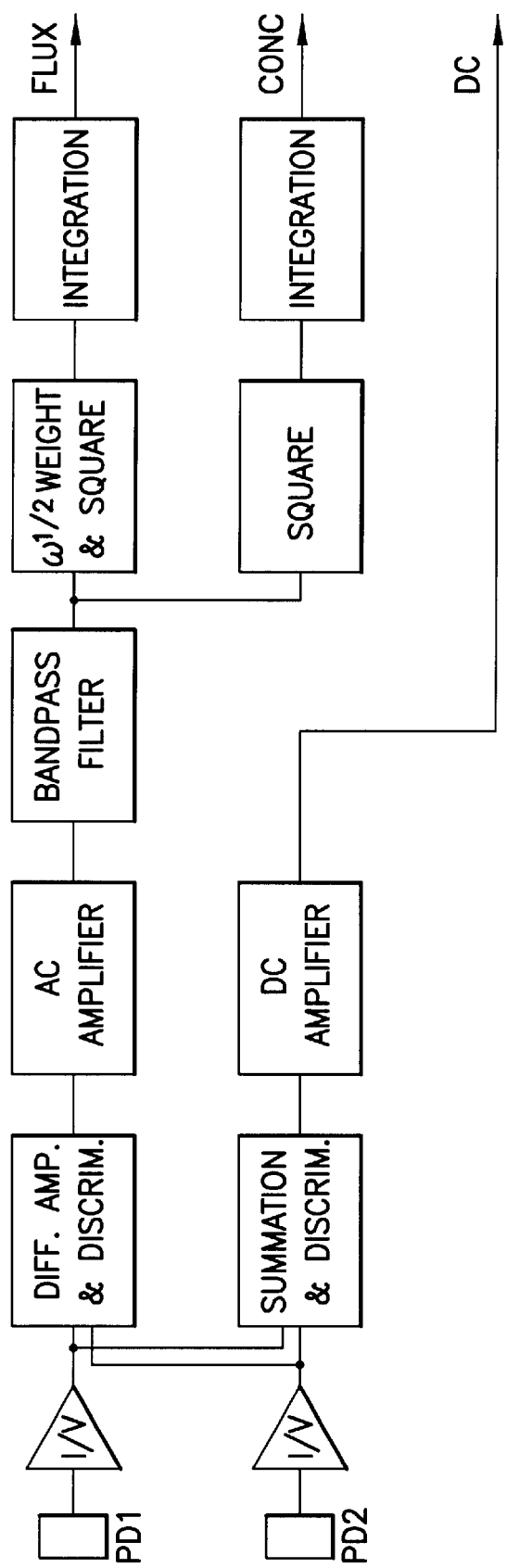
FIG. 9 is a system diagram of processing electronics for processing the photodiode currents from two photodiodes using (a) analogue processing or (b) digital processing.
Figure 9B:
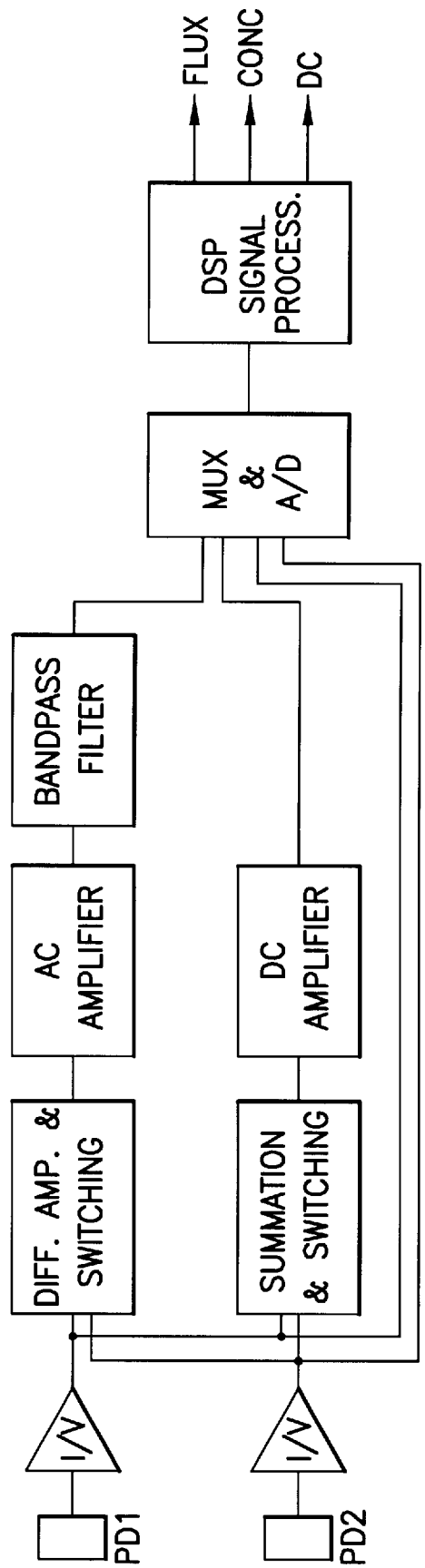
Figure 10A:
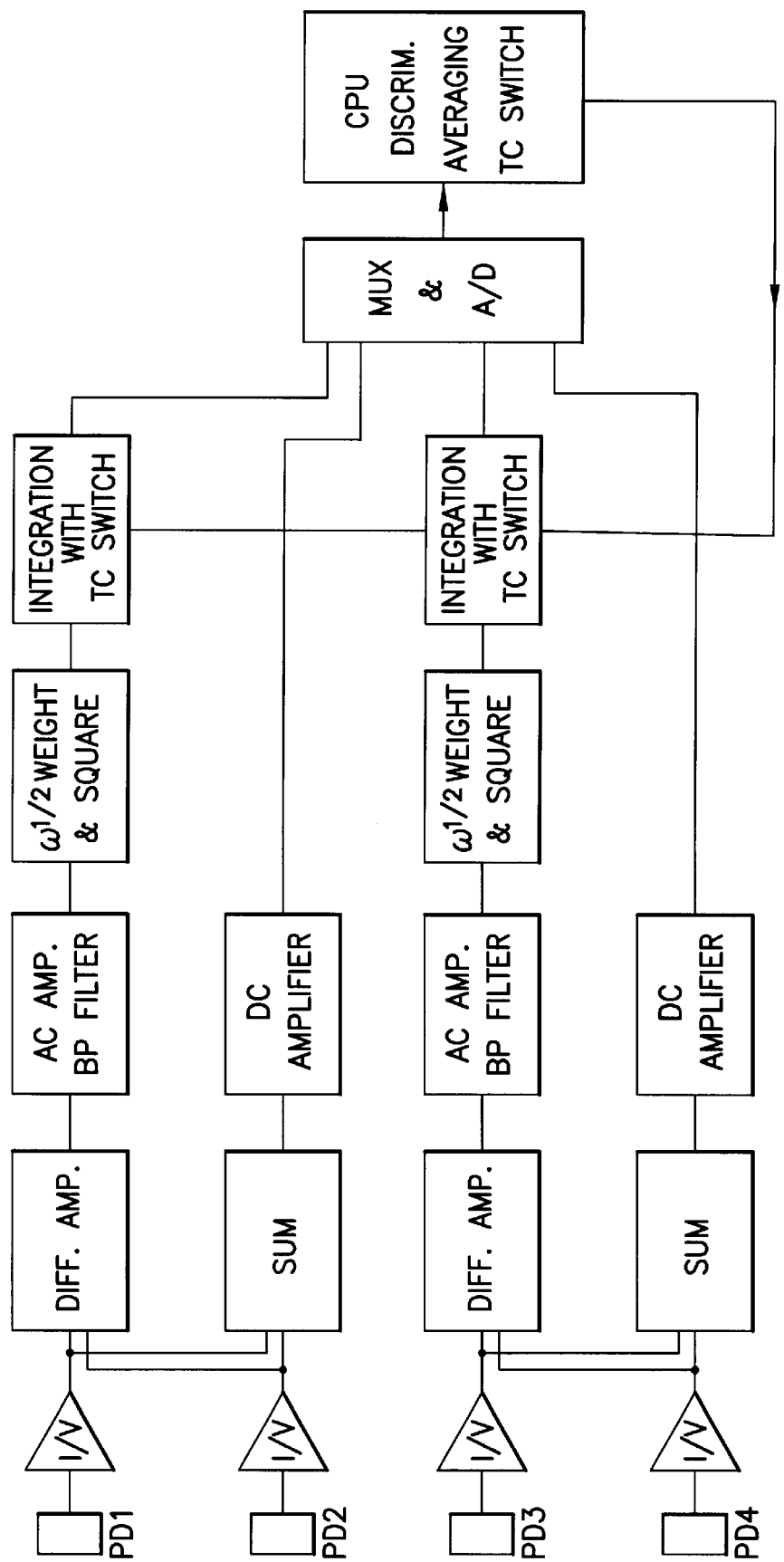
FIG. 10 is a system diagram of processing electronics for processing the photodiode currents from four photodiodes using (a) analogue processing or (b) digital processing.
Figure 10B:
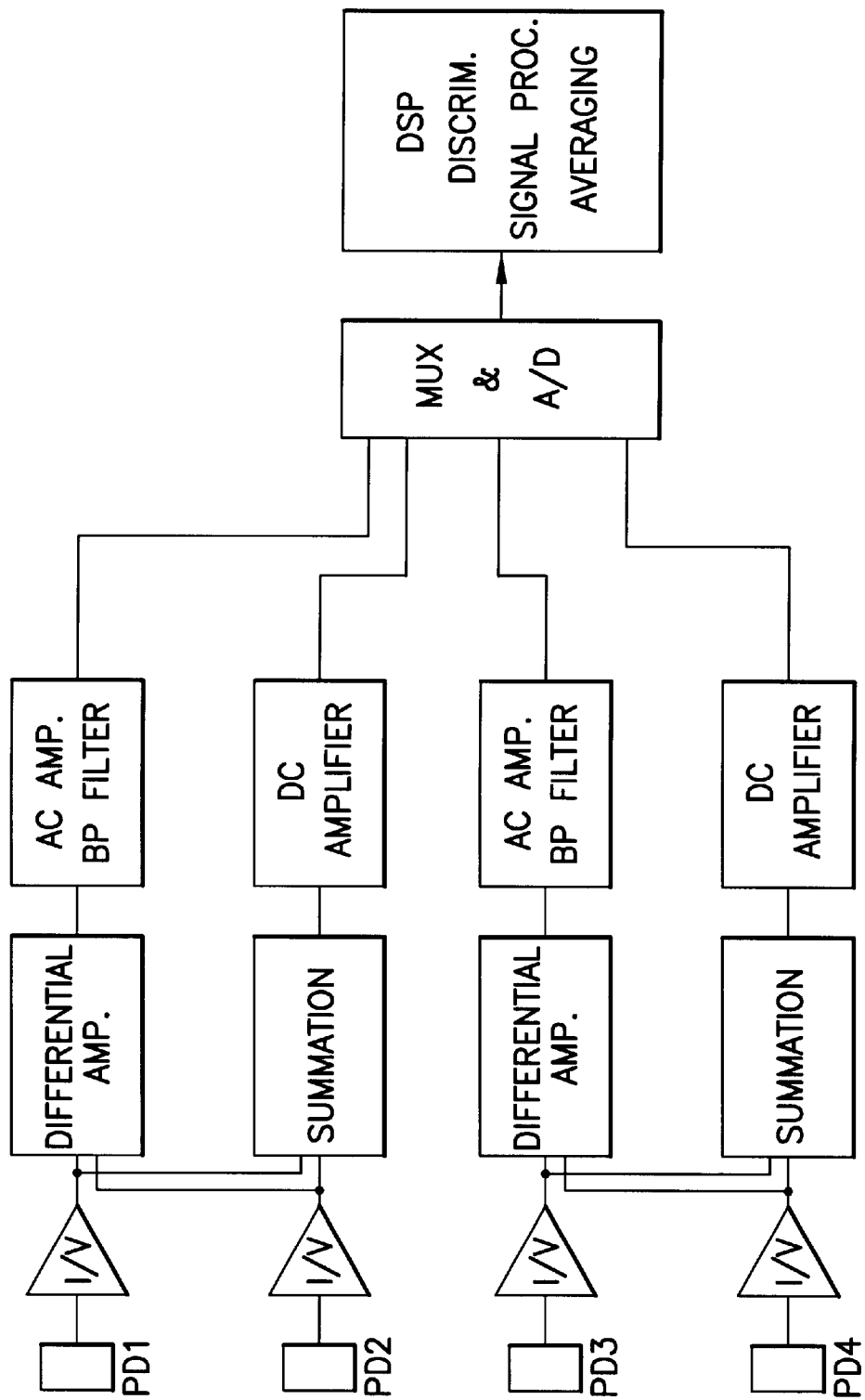

For example, if measurements are being made at 10 ms intervals a time constant of a few ms is used. FIG. 9 is a system diagram for an analogue system using two photodectors and FIG. 10a is for a system using four photodetectors. The systems FIG. 9b and FIG. 10b are DSP systems described below.

Noise subtraction and normalisation can be carried out by analogue circuits or in a digital processor after the flux analogue signal has been converted to a digital signal via an A/D converter.

An alternative method of processing would be to use mainly digital processing. This would preferably employ the technique of Fast Fourier Transformation (FFT), implemented with fast digital signal processor (DSP) ICs, to calculate Flux. This alternative method requires filtering to separate the dc and ac components of the photo current after current to voltage conversion, analogue to digital conversion, and processing by a DSP IC. If the A/D and DSP are sufficiently fast photo current signals from several photodetectors can be processed to generate flux and $I_{dc}$ values at high data rates (e.g., 40 Hz). If higher data rates or more channels are required DSP ICs can be operated in parallel.

The basic algorithm that is implemented is $$\text{Flux} = \int_{\omega_1}^{\omega_2} \omega P(\omega) d\omega = \sum_{n_1}^{n_2} n F(n)^2 = \sum_{n_1}^{n_2} n P(n)$$

where n $\alpha$ $\omega$ and F(n) is the amplitude of the Fourier component at a 'frequency' n. A fast FFT algorithm using decimation in frequency is utilised in the above DSP calculation. Noise subtraction and normalisation are performed in the DSP.

According to a preferred embodiment the apparatus will include means for producing an image of the blood perfusion in the tissue from the processed output signals and means for producing a photoimage from variations in the intensity of the detected scattered light. This allows the flux image or part of the image to be superimposed on the photographic image. Even more preferred is that the apparatus additionally includes means for producing a video image of the tissue section irradiated. If combined with means for superimposing the image of the blood perfusion on the video image it is possible to show and record the location and appearance of the tissue surface. The video image will be produced from visible light reflected by the tissue section being imaged on a CCD camera or using a camcorder with a video image frame grabber and both the blood perfusion image and live video image may then be displayed on a monitor simultaneously.

What is claimed is:

1. An apparatus for imaging blood perfusion in tissue comprising:

a monochromatic laser light source;

means for irradiating a section of the surface of the tissue with monochromatic light from the light source;

means for collecting light scattered from the irradiated section;

means for scanning a beam of the monochromatic laser light over the tissue surface in a predetermined pattern;

means for scanning the beam at substantially constant speed across the tissue;

means for determining and recording the position of the beam at any point of the scan;

means for halting the beam at a predetermined position or positions during the scan;

two or more photodetectors for positioning to collect light diffusely scattered from the tissue surface and for positioning to ensure that specularly reflected light is detected by either no detector or by only one detector at a given time;

means for processing the electrical output signals from the photodetectors;

means for registering saturation of a photodetector and eliminating the saturated photodetector signal from signal processing; and means for recording and displaying the blood perfusion measurements.

2. An apparatus according to claim 1, comprising means for producing an image of the blood perfusion in the tissue from the processed output signals and means for producing a photoimage from variations in the intensity of the detected scattered light.

3. An apparatus according to claim 1, which additionally comprises means for producing a video image of the tissue section irradiated.

4. An apparatus according to claim 3 wherein there is also provided means for superimposing the image of the blood perfusion on the video image on a display means.

5. An apparatus according to claim 1, wherein two pairs of photodiodes are used to collect the light diffusely scattered from the tissue surface.

6. An apparatus for imaging blood perfusion in tissue comprising:

a monochromatic laser light source;

means for irradiating a section of the surface of the tissue with monochromatic light from the light source;

means for collecting light scattered from the irradiated section;

means for scanning a beam of the monochromatic laser light over the tissue surface in a predetermined pattern;

means for scanning the beam at substantially constant speed across the tissue;

means for determining and recording the position of the beam at any point of the scan;

means for halting the beam at a predetermined position or positions during the scan;

two pairs of photodetectors for positioning to collect light diffusely scattered from the tissue surface to provide a system having two independent channels and for positioning to ensure that specularly reflected light is detected by either no detector or by only one detector at a given time;

means for processing the electrical output signals from the photodetectors;

means for storing and displaying both of the flux images generated by the two channels;

means for processing said flux images and eliminating regions of saturation from the images; and means for combining the images to produce a saturation free blood flow image.

7. An apparatus according to claim 2, which additionally comprises means for producing a video image of the tissue section irradiated.

8. An apparatus according to claim 2, wherein two pairs of photodiodes are used to collect the light diffusely scattered from the tissue surface.

9. An apparatus according to claim 3, wherein two pairs of photodiodes are used to collect the light diffusely scattered from the tissue surface.

10. An apparatus according to claim 4, wherein two pairs of photodiodes are used to collect the light diffusely scattered from the tissue surface.

* * * * *